US008857440B2

(12) United States Patent
Gundlapalli et al.

(10) Patent No.: US 8,857,440 B2
(45) Date of Patent: Oct. 14, 2014

(54) DEVICES AND METHODS FOR PROTECTING TISSUE AT A SURGICAL SITE

(75) Inventors: RamaRao Gundlapalli, Leesburg, IN (US); Matthew Smith, Akron, IN (US); Mark Heldreth, Mentone, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 2690 days.

(21) Appl. No.: 10/873,738

(22) Filed: Jun. 22, 2004

(65) Prior Publication Data

US 2005/0283050 A1 Dec. 22, 2005

(51) Int. Cl.
| | | |
|---|---|---|
| *A61B 19/08* | (2006.01) | |
| *A61F 13/06* | (2006.01) | |
| *A61B 17/02* | (2006.01) | |
| *A61B 17/34* | (2006.01) | |
| *A61B 19/00* | (2006.01) | |

(52) U.S. Cl.
CPC ....... *A61B 17/3423* (2013.01); *A61B 2019/481* (2013.01); *A61B 2019/085* (2013.01); *A61B 17/0293* (2013.01); *A61B 19/08* (2013.01)
USPC ............................................. 128/850; 602/62

(58) Field of Classification Search
USPC .............. 128/849, 850, 852, 853, 854; 40/27, 40/673; 428/136; 600/208; 602/62
See application file for complete search history.

(56) References Cited

U.S. PATENT DOCUMENTS

| | | | | |
|---|---|---|---|---|
| 3,332,417 A | * | 7/1967 | Blanford et al. .............. | 128/850 |
| 3,347,226 A | | 10/1967 | Harrower | |
| 3,397,692 A | * | 8/1968 | Creager, Jr. et. al. .......... | 128/850 |
| 3,416,520 A | * | 12/1968 | Creager, Jr. .................... | 128/850 |
| 3,522,800 A | * | 8/1970 | Lesser ............................ | 600/206 |
| 3,669,106 A | * | 6/1972 | Schrading et al. ............. | 128/853 |
| 3,750,664 A | * | 8/1973 | Collins .......................... | 128/853 |
| 3,882,859 A | * | 5/1975 | Ericson ......................... | 128/854 |
| 4,114,624 A | * | 9/1978 | Haverstock ................... | 606/167 |
| 4,534,768 A | * | 8/1985 | Osburn et al. ................. | 604/350 |

(Continued)

FOREIGN PATENT DOCUMENTS

| | | |
|---|---|---|
| WO | WO 00/54677 | 9/2000 |
| WO | WO 03/061480 | 7/2003 |

OTHER PUBLICATIONS

"Space-OR . . . An Innovative Solution to Internal Organ Retraction", Advanced Surgical Concepts ©2000, (4 pages).

(Continued)

*Primary Examiner* — Heidi M Eide
(74) *Attorney, Agent, or Firm* — Maginot, Moore & Beck, LLP (57) ABSTRACT

A tissue protector is adapted to be positioned on the skin surrounding an incision. The tissue protector provides a load bearing surface for surgical tools and instruments to prevent blunt force and pressure trauma to the skin and soft tissues within the incision. In one embodiment, the tissue protector is a sheet of wear-resistant material having an opening corresponding to the incision and expandable as the incision is retracted. In another embodiment, a tissue protector device includes a continuous expandable arrangement of interconnected L-shaped links. In still another embodiment, a one-piece tissue protector includes a flexible panel supported on the skin and a flexible sleeve extending into the incision. Yet another embodiment of the invention resides in a track that is supported about the incision. An instrument support platform is slidably mounted to the track to support a surgical tool relative to the incision.

18 Claims, 8 Drawing Sheets

(56) References Cited

U.S. PATENT DOCUMENTS

| | | | |
|---|---|---|---|
| 4,650,705 A * | 3/1987 | Ghodsian | 428/40.6 |
| 4,727,868 A * | 3/1988 | Szycher et al. | 602/43 |
| 4,899,762 A * | 2/1990 | Muller | 128/850 |
| 5,366,478 A | 11/1994 | Brinkerhoff et al. | |
| 5,524,644 A | 6/1996 | Crook | |
| 5,649,550 A | 7/1997 | Crook | |
| 5,810,721 A | 9/1998 | Mueller et al. | |
| 5,897,517 A * | 4/1999 | Laghi | 602/62 |
| 5,906,577 A | 5/1999 | Beane et al. | |
| 5,957,913 A | 9/1999 | de la Torre et al. | |
| 5,985,395 A * | 11/1999 | Comstock et al. | 128/855 |
| 6,024,736 A | 2/2000 | de la Torre et al. | |
| 6,048,309 A | 4/2000 | Flom et al. | |
| 6,142,935 A | 11/2000 | Flom et al. | |
| 6,142,936 A | 11/2000 | Beane et al. | |
| 6,149,642 A | 11/2000 | Gerhart et al. | |
| 6,171,236 B1 | 1/2001 | Bonutti | |
| 6,187,023 B1 | 2/2001 | Bonutti | |
| 6,254,533 B1 | 7/2001 | Fadem et al. | |
| 6,254,534 B1 | 7/2001 | Butler et al. | |
| 6,315,770 B1 | 11/2001 | de la Torre et al. | |
| 6,319,246 B1 | 11/2001 | de la Torre et al. | |
| 6,382,211 B1 | 5/2002 | Crook | |
| 6,440,063 B1 | 8/2002 | Beane et al. | |
| 6,450,983 B1 | 9/2002 | Rambo | |
| 6,578,577 B2 | 6/2003 | Bonadio et al. | |
| 6,582,364 B2 | 6/2003 | Butler et al. | |
| 6,615,837 B1 * | 9/2003 | Griesbach, III | 128/849 |
| 6,647,985 B1 * | 11/2003 | Prywes | 128/853 |
| 6,694,981 B2 * | 2/2004 | Gingles et al. | 128/849 |
| 6,705,324 B1 * | 3/2004 | Petersvik | 128/849 |
| 6,814,078 B2 * | 11/2004 | Crook | 128/849 |
| 6,863,071 B2 * | 3/2005 | Annett et al. | 128/849 |
| 6,939,296 B2 * | 9/2005 | Ewers et al. | 600/206 |
| 2002/0169431 A1 * | 11/2002 | Kline et al. | 604/385.03 |
| 2003/0191424 A1 * | 10/2003 | Skinner | 128/856 |
| 2004/0003817 A1 * | 1/2004 | Annett et al. | 128/849 |
| 2004/0015185 A1 | 1/2004 | Ewers et al. | |
| 2004/0054353 A1 | 3/2004 | Taylor | |

OTHER PUBLICATIONS

Background Tissue Necrosis and Pressure, http://www.medicaledu.com/pressure.htm, Aug. 25, 2003, (17 pages).

* cited by examiner

DEVICES AND METHODS FOR PROTECTING TISSUE AT A SURGICAL SITE

BACKGROUND OF THE INVENTION

The present invention relates to devices and methods for protecting the skin and soft tissues at a surgical site, and more specifically surrounding an incision. This invention is particularly useful in conjunction with minimally invasive surgery or minimal incision surgery.

In traditional open surgeries, a large incision is utilized to access the surgical site and provide a wide field of vision. In these types of surgeries, an incision of 7-8 inches is commonplace, as are incisions through the large musculature. Joint replacement surgeries are particularly suited for an open surgery since the surgeon must identify particular bony landmarks, perform osteotomies and properly position and affix the components of a joint endoprosthesis.

However, in recent years, minimally invasive techniques have been adapted to joint replacement surgeries. Minimal incisions are becoming increasingly popular among patients, especially where the surgical scar will be very visible. Moreover, minimally invasive techniques reduce the need to disturb the musculature, which can significantly reduce healing and rehabilitation time following joint replacement.

Notwithstanding the surgical approach, the surgeon must still properly identify bony landmarks that are critical to proper positioning of the joint endoprosthesis. Thus, even when a minimal incision (i.e., an incision less than 7 inches long) is employed, something must be done to allow the surgeon to recognize the appropriate features and properly place the implant relative to those features.

Where the length of the incision limits surgical site visibility, a common practice has been to stretch the incision to thereby increase the area of the opening. The skin and adjacent soft tissues are routinely stretched to their elastic limits. For instance, a 3 inch incision is often stretched to 5-6 inches. Tissue retractors are used to help stretch the incision, as well as to move adjacent soft tissues aside to permit unimpeded viewing of the joint to be replaced. Due to the small incision, and in order to obtain the required exposure, a great deal of leverage or force is applied to the surrounding soft tissues, to stretch the incision using retractors and to elevate the bones of the joint using other instruments.

It has been found that high pressure over long periods of time can lead to necrosis of the skin and the soft tissue surrounding the incision. In tissue tests, a medical pressure sensor (such as an intra-cranial pressure sensor) was placed within a muscle laterally offset from the center of an incision. Pressure measurements are made when retractors are initially positioned within the incision and thereafter as the incision was expanded. It was found that the pressure increased to a magnitude nearly five times greater than the pressure on the wound when the retractors were initially introduced. Thus, with an initial wound pressure of about 20 mmHg, the pressure increased to about 100 mmHg when the incision was fully retracted. This value is within the range of pressures that have been found to produce necrosis in the soft tissues adjacent the incision.

In addition, frictional and shearing forces generated by tools acting against the tissue have been found to contribute to tissue lacerations or necrosis. At a minimum, the pressure exerted on the soft tissues can result in significant discoloration and discomfort to the patient. At the other extreme, the tissue can become necrotic, with the concomitant risk of non-healing and infection. These negative aspects can sometimes negate the benefits of minimal incision or minimally invasive surgical techniques.

As minimally invasive techniques become more prevalent, especially in the field of joint repair and replacement, the need to protect the skin and adjacent soft tissue becomes more acute. Intra-operative wound protection can form a critical prong in an overall wound management program that includes pre-operative treatment, intra-operative and post-operative protocols. Most wound management programs are directed to controlling infection. The major causes of wound infection is by two organisms—Staph Aureus and Staph Epidermidis, skin dwelling organisms that are easily drawn into a wound from the exposed skin by surgical instruments. A pre-incision protocol includes cleaning the skin with a germicide wipe and providing an incision sheet, such as an iodine sheet. A post-operative protocol includes periodically cleaning the wound and applying an anti-infection compound, such as Triclosan, silver ions or chlorhexidine. Post-incision protocols also address non-healing problems, such as by the use of collagen seeds or scaffolds, and pain management issues.

While most of the wound management protocols have focused on pre- and post-incision or operative care, there remains a significant need for wound management during the surgical procedure. Thus, there is a significant need for devices and methods that can protect these tissues during retraction of an incision and throughout the surgery.

SUMMARY OF THE INVENTION

The present invention addresses this need with a tissue protector in one embodiment that comprises a sheet of abrasion-resistant material defining an elongated opening for access to a tissue incision. The sheet has an adherent facing surface adapted to be applied to the surgical site surrounding the incision. In certain embodiments, the sheet further includes a bead defined around at least a portion of the opening. The bead is arranged to support a surgical tool or instrument extending into the incision when the sheet is applied to the surgical site.

The abrasion-resistant sheet of material can be anisotropic so that it exhibits greater resistance to stretching along an axis parallel to the length of the elongated opening than along an axis perpendicular to the length. The sheet can further include an expandable portion spanning the elongated opening at opposite ends thereof. This expandable portion includes a pleat and can be configured to expand less toward the terminal ends of the opening. Reinforcements can be formed at the opposite ends of the elongated opening.

In another embodiment of the invention, a tissue protector device for use in minimally invasive surgery comprises a plurality of generally L-shaped links, each sized for contacting a portion of a surgical incision, and means for connecting adjacent links of the plurality of links to permit expansion of the distance between the plurality of links. The plurality of links includes a first set of links and a second set of links alternatingly disposed between links of the first set, and the means for connecting includes a sliding connection between links of the first set and links of the second set to permit relative movement therebetween. The sliding connection includes a male-female connection between links of the first set and links of the second set.

In certain embodiments, the male-female connection includes a channel defined in links of the first set of links, the channel configured to slidably receive links of the second set of links therein. The links of the first set of links can be generally tubular.

In one feature of this embodiment, the sliding connection includes a slot defined in links of the first set of links and a protrusion connected to links of the second set of links and extending into the slot to slide within the slot. The slot can include a detent at the opposite ends of the slot, each the detent offset from the slot so that the protrusion is prevented from sliding within the slot when the protrusion is disposed within the detent.

In a specific embodiment, the plurality of links are connected to form a continuous circle. The means for connecting is operable to permit expansion of the continuous circle from a first diameter to a larger second diameter. In another specific embodiment, the plurality of links are connected to form at least two opposing arc segments. The opposing arc segments can be elliptical so that the connected segments form an elliptical or oblong shape to emulate the periphery of the retracted incision. A hinge can be provided connecting at least one end of each of the opposing arc segments. In one aspect, the hinge is resiliently biased to pivot the opposing arc segments away from each other.

A tissue protector in another embodiment of the invention comprises a flexible panel having a facing surface adapted to be supported on the skin adjacent an incision. The panel defines an opening for alignment over the incision when the panel is supported on the skin. A flexible sleeve is substantially coextensive with the opening and extends from the facing surface to extend into the incision when the facing surface is supported on the skin. In one feature of this embodiment, the flexible sleeve and the flexible panel are integral.

The flexible sleeve includes an upper edge integral with the flexible panel at the opening and a lower edge flared outwardly relative to the upper edge. The opening in the flexible panel is elongated in a generally oval shape. The upper surface of the flexible panel defines at least one continuous rib concentrically disposed about the opening. The ribs dissipate the loads applied to the tissue protector by tools and instruments during the surgical procedure. The flexible sleeve also includes at least one circumferential rib spaced apart from the opening on an interior surface of the sleeve.

In still another embodiment of the invention, a tissue protector device for minimally invasive surgery comprises a track configured to encircle at least a portion of an incision at a surgical site and an instrument platform having an upper surface for supporting an instrument. The platform includes an opposite lower surface with means between the lower surface and the track for slidably mounting the instrument platform on the track with the upper surface aligned with the incision. The device can include means for fixing the location of the track relative to the incision. This means for fixing can include a panel attached to the track, the panel including an adherent facing surface adapted to be applied to the surgical site surrounding the incision and defining an opening for access to the incision.

The means for slidably mounting can be configured to permit pivoting of the instrument platform relative to the track. In a preferred embodiment, the means for mounting includes a bracket projecting from the lower surface, the bracket defining a notch configured to engage the track. The track includes an upper ring having a substantially circular cross-section, so that the notch can be substantially circular to engage the upper ring.

The upper surface of the instrument platform defines a channel for receiving the instrument. The channel can include an elongate arcuate surface. The platform can also include a deflector panel at an end of the upper surface, the deflector panel being oblique to the upper surface, to help guide the surgical instrument onto the platform.

In certain embodiments of the invention, the material of the tissue protector is formed of an absorbent or adsorbent material. The material can be a fabric or fabric-like material dosed with an anti-infection compound. For instance, the material can be initially immersed in an anti-infection bath, such as Triclosan. Alternatively, a solid material, such as silver ion particles or fibers, can be interwoven into the fabric material. For non-fabric materials the anti-infection compound can be used to coat the material of the tissue protector. As a further alternative, a strip of material soaked in an anti-infection compound can be applied to the tissue protectors of the present invention.

One aspect of the invention contemplates a device for protecting body tissues at an incision that comprises a first portion configured to be supported on body tissues surrounding the incision and a second portion associated with the first portion and configured to cover body tissues within the incision. In one specific embodiment, the first portion includes a flexible panel having a facing surface adapted to be supported on the body tissues surrounding the incision. The panel defines an opening for alignment over the incision. In this embodiment, the second portion includes a flexible sleeve integral with the first portion and substantially coextensive with the opening. The sleeve projects from the facing surface to extend into the incision to cover body tissues within the incision.

In another specific embodiment incorporating this feature, the first portion and the second portion are integral to form an L-shaped body. One portion of the L-shaped body is supported on the body tissues surrounding the incision, while the other portion of the L-shape extends into the incision to cover body tissues within the incision.

Yet another feature of the invention contemplates a device for protecting body tissues at an incision that comprises a first portion configured to be supported on body tissues surrounding the incision and means carried by the first portion for dissipating forces applied thereon by a surgical tool or instrument introduced into the incision. With this feature, the load that would normally be directly applied to the body tissues around and within the incision is dissipated by the device to minimize the local loading on the body tissues. In one specific embodiment, the first portion includes a sheet of material defining an elongated opening for access to the incision and the means for dissipating forces includes a bead defined on the sheet adjacent and around the elongated opening.

In another specific embodiment, the device further comprises a second portion integral with the first portion and substantially coextensive with the opening. The second portion projects from the first portion to extend into the incision to cover body tissues within the incision. In yet another specific embodiment of this inventive feature, the means for dissipating forces includes a second portion integral with the first portion to form an L-shaped body configured to engage the incision.

It is one object to provide devices and methods for protecting the soft tissue adjacent an incision from trauma associated with the use of surgical instruments through the incision. It is a further object to provide devices that can help support the surgical instruments during the procedure. Other objects and certain benefits of the invention will become apparent from the following written description and accompanying figures.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figures 1, 2, 3:
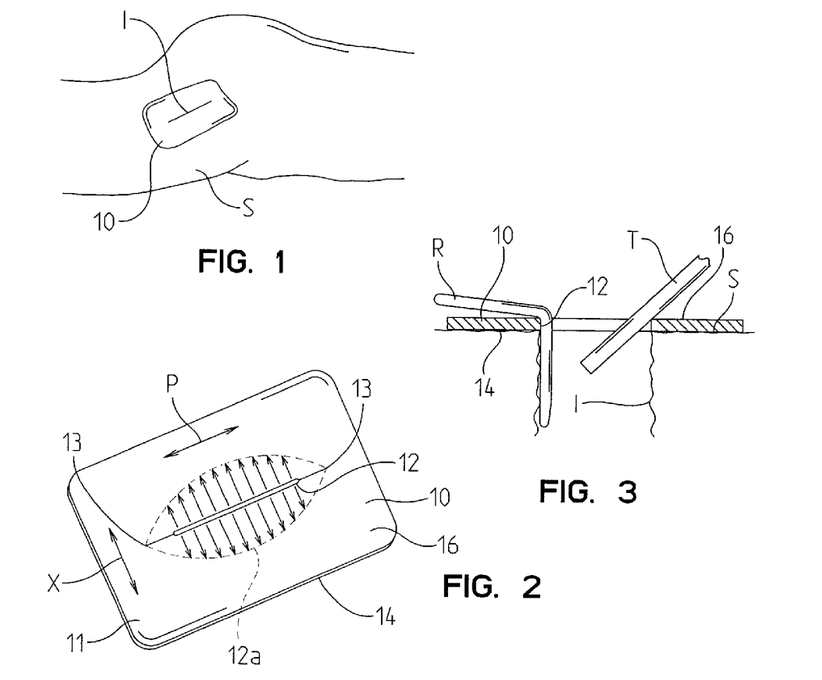
FIG. 1 is a side view of a surgical site for surgery on the hip joint with a tissue protector according to one embodiment of the invention.
FIG. 2 is an enlarged top perspective view of the tissue protector shown in FIG. 1.
FIG. 3 is an enlarged cross-sectional view of an incision with the tissue protector of FIG. 2 associated therewith.

The present invention is particularly suited for minimally invasive surgery, and most particularly for joint surgery. For instance, the tissue protector 10 of one embodiment of the invention is associated with a surgical site S at a joint of a patient. For illustrative purposes, the joint is the hip joint, where minimally invasive procedures are often problematic due to tissue thickness surrounding the joint. The surgical procedure can be a joint replacement in which the acetabular and the proximal femoral components are replaced with corresponding endoprosthesis components. The tissue protector 10 surrounds the incision I, which will typically be a minimal incision of less than 6 inches.

The tissue protector 10 includes a sheet 11 of an abrasion or wear-resistant material. For instance, the sheet material can include a non-woven fabric comprising a web of cellulose fibers and polyester/polyethylene conjugate fibers interspersed throughout the cellulose fiber web. In one specific embodiment, the sheet 11 is formed from polyurethane, while in other specific embodiments the material can be proprietary wear-resistant materials, such as BIOINCLUSIVE™ sold by Johnson & Johnson, Inc., or CORDURA® sold by Invista, Inc. The material of the sheet 11 must be sufficiently wear-resistant so that the material does nor break down or erode under pressure or abrasion from surgical instruments continuously bearing against and sliding across the sheet during a surgical procedure.

A slot 12 is defined in the sheet 11 that is initially closed but that expands to define a wider opening 12a as the surgical incision I is retracted or stretched in the direction of the multiple arrows. As shown in FIG. 3, it is contemplated that the sheet 11 will be situated relative to the incision I so that the slot 12 is at least coincident with the incision, and preferably at least slightly overhanging the incision. The tissue protector 10 thus forms a wear-resistant barrier between the tissue at the surgical site S and a surgical instrument T. The tissue protector sheet 11 also protects the skin against the pressure of the tissue retractor R.

In a preferred embodiment, the slot 12 is preformed in the sheet 11. Alternatively, the sheet can be provided intact and the slot formed with the incision I at the surgical site. With this alternative, the sheet 11 is formed of a material that can be readily cut with a scalpel without disturbing the integrity and abrasion-resistance of the sheet. Where the material of the sheet has a "grain", the grain is preferably aligned in the direction of the incision.

Figure 4:
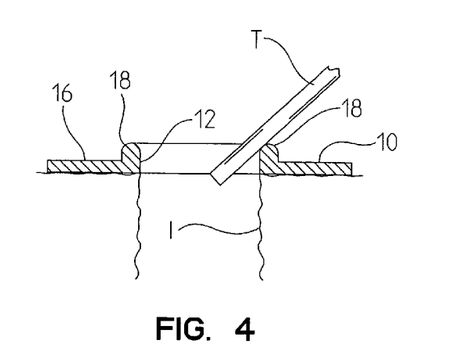
FIG. 4 is an enlarged cross-sectional view of an incision with a tissue protector modified from the embodiment shown in FIG. 2.

In a variation of this embodiment, the sheet 11 can define an enlarged bead 18 around substantially the entire perimeter of the slot 12. This bead projects from the upper surface 16 to provide a raised surface for supporting a surgical tool T. The bead 18 also provides a region of increased thickness, and therefore increased wear-resistance. The bead 18 can also be formed at the inner perimeter of the opening 12, or can extend into or below the opening. This feature may be valuable where the tissue protector is formed of a sterilizable and reusable material. The bead 18 also serves as a means for dissipating forces applied by a surgical tool or instrument. As explained above, it has been found the force applied to body tissues by surgical tools and instruments can be significant, often high enough to risk necrosis. Thus, this feature of the invention allows the normal tool or instrument loads to be dissipated through the bead 18 and sheet 11 to reduce or eliminate this localized loading of the body tissues.

In one aspect of one embodiment of the invention, the sheet 11 of the tissue protector 10 exhibits anisotropic properties. In other words, the sheet 11 exhibits greater resistance to stretching in a direction P parallel to the slot 12 (and the incision I) than in a direction X that is transverse to the slot. Thus, the sheet can stretch in the direction X as the tissue retractor R engages the incision I, as shown in FIG. 3.

Figure 5:
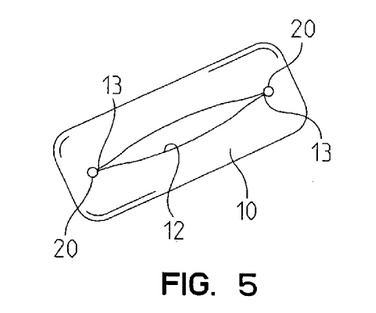
FIG. 5 is an enlarged top perspective view of a further modification of the tissue protector shown in FIG. 2.

In one specific embodiment, the sheet 11 is formed of two sheets separated along the slot 12. However, the preferred form of the tissue protector 10 is a single sheet of material. In a variation of this embodiment, a reinforcement 20 can be formed at the ends 13 of the slot 12. The reinforcement 20 can consist of a bead of material affixed to the sheet 11 or can constitute a treatment of the sheet at the slot ends 13, such as melting or fusing. The reinforcements 20 resist tearing of the sheet material when the slot 12 is laterally stretched to its expanded configuration 12a. In addition, the reinforcements may also act as a physical stop to the amount of stretch of the sheet, thus providing a limiting parameter prior to damage of the tissue at the incision.

Figure 6:
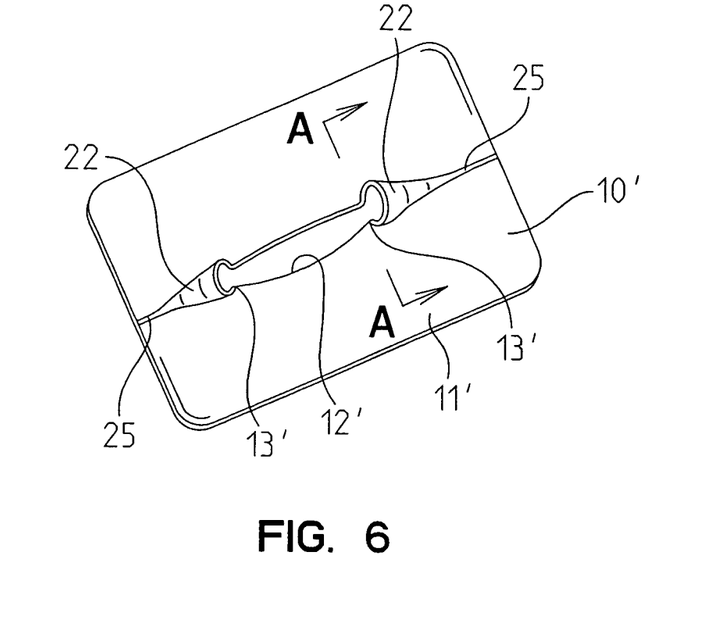
FIG. 6 is an enlarged top perspective view of another modification to the tissue protector of FIG. 2.
Figure 7:
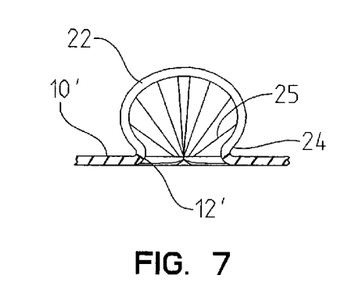
FIG. 7 is an enlarged partial cross-sectional view of the modified tissue protector of FIG. 6, taken along line A-A as viewed in the direction of the arrows.

Referring to FIGS. 6 and 7, yet another variation of the tissue protector 10 is illustrated. In particular, a modified tissue protector 10' includes a sheet 11' that defines a slot 12', similar to the previous embodiment. However, with this variation, the sheet 11' includes expandable portions 22 at the ends 13' of the slot 12'. The expandable portions 22 provide a mechanism for accommodating additional stretch as the incision I and the slot 12' are expanded in the stretch direction (see FIG. 2). In a preferred embodiment, the expandable portions 22 are formed by a pleat 24 in the sheet 11', as best depicted in FIG. 7. The pleat 24 is, in essence, an area of excess or loose material spanning the slot 12'. As the slot 12' expands, the width of the slot reaches a point where the pleat 24 is consumed and the material of the pleat is placed in tension to resist further expansion. In a specific embodiment, the pleat 24 is tapered to a reduced pleat 25 at the outermost ends of the slot 12'. The tapered pleat recognizes that the tissue protector 10' will expand with the incision I to a generally oval shape. Consequently, the expandable portion 22 expands less towards the ends of the slot 12'.

Figure 6A:
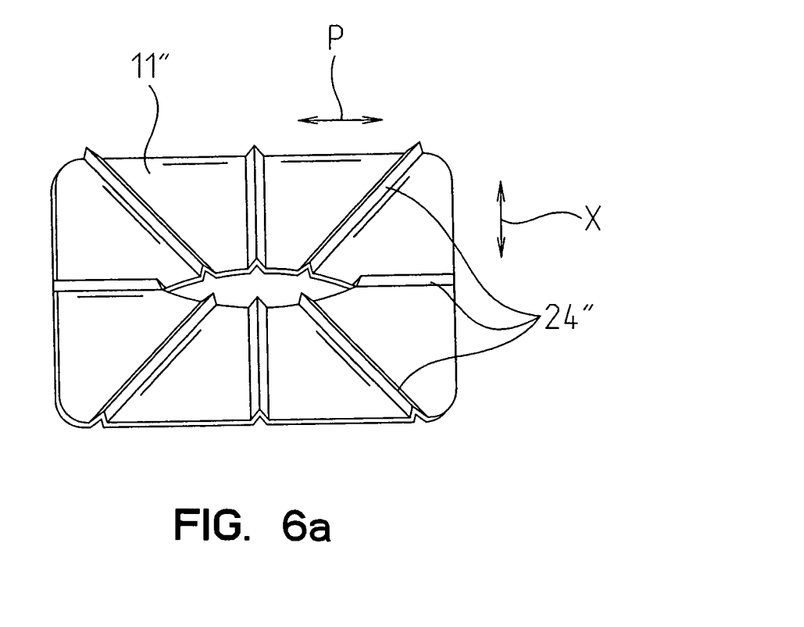
FIG. 6a is an enlarged top perspective view of a modification of the tissue protector shown in FIG. 6.

While the preferred embodiment contemplates the use of pleats 24 for the expandable portion, other configurations are contemplated. For instance, the sheet can include multiple pleats in different directions to accommodate stretching along multiple axes, as shown in FIG. 6a. In this embodiment, the sheet 11'' includes several pleats 24'' arranged at different orientations, some parallel to one of the axes X and P and others at angles to these axes.

In yet another alternative embodiment, the sheet 11' can include a portion of material that can be stretched in the transverse direction X (see FIG. 2). This approach is well-suited for an embodiment in which the sheet 11' is formed of two adjacent sheets, spaced apart to form the slot 12'. Alternatively, the sheet can also be stretched in the parallel direction P, as shown in FIG. 2, although the degree of parallel stretch is nominally less than the stretch in the transverse direction X.

Figure 8:
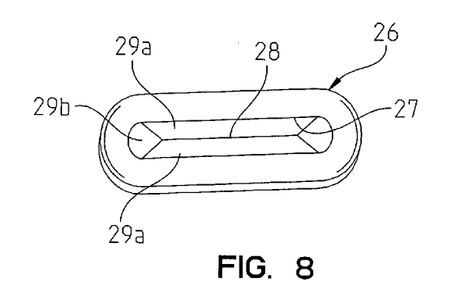
FIG. 8 is a top perspective view of a further modification to the tissue protector shown in FIG. 2.

In an additional variation of the sheet tissue protector embodiments, a tissue protector sheet 26 can include flaps 29a and 29b that fold along a fold line 27 that defines the opening of the sheet 26. The interior edges of the flaps define the slot 28 that opens when the flaps are folded downward into the incision I. The sheet 26 can exhibit the same anisotropic properties discussed above to permit expansion of the sheet opening as the incision is retracted. When the flaps 29a, 29b are opened and folded downward into the incision, they will protect the interior tissue against excessive pressure exerted by retractors R and instruments T.

In all of the variations of FIGS. 1-8, the tissue retractor sheet preferably includes an adherent facing surface. Thus, referring back to FIGS. 2-3, the sheet 11 includes a facing surface 14 opposite the upper surface 16. The facing surface is coated with a medically acceptable, self-adhering layer. The adhesive layer can be configured to removably adhere directly to the skin at the surgical site S, or to adhere to an antiseptic film, such as butadiene, applied around the incision.

In a method of the present invention, the surgical site is cleaned and the butadiene film applied. The incision can be made prior to or after application of the tissue protector. In one embodiment, the slot 12 is formed in the tissue protector sheet 11 when the incision is made. However, in the most preferred embodiment, the incision is made and the joint capsule partially exposed before the tissue protector is applied with the slot 12 coinciding with the mouth of the incision I. Tissue retractors R can then be introduced to open the incision to further expose the joint. The surgeon uses the necessary tools T to retract the soft tissue surrounding the bony landmarks that must be identified. The entire surgical procedure can continue using various surgical tools and instruments with any of the tissue protectors of the embodiments shown in FIGS. 1-8 in position around the incision I. The material of the tissue protector sheets will prevent abrasion or excessive pressure on the skin at the surgical site S and underlying soft tissue.

In certain specific embodiments, the sheet is formed of an absorbent or adsorbent material. The material can be an fabric or fabric-like material dosed with an anti-infection compound. For instance, the material can be initially immersed in an anti-infection bath, such as Triclosan. Alternatively, a solid material, such as silver ion particles or fibers, can be interwoven into the fabric material. For non-fabric materials the anti-infection compound can be used to coat the sheet of material.

In an alternative embodiment of the invention, a tissue protector device 30 is provided that can expand to an infinitely variable range of dimensions, as depicted in FIGS. 9-12. The tissue protector device 30 is formed by a plurality of interconnected links, provided in a first set of links 32 and a second set of links 34. Means are provided for connecting links of the first set 32 to links of the second set 34 so that the distance between links can be changed, or expanded, in the direction of the arrows E in FIG. 9. In the preferred embodiment, this means includes a slot 38 defined in the links 34 of the second set. The slots receive pins 40 that pass through bores 41 at the ends of the links 32 of the first set. The pins 40 are sized to slide freely within a corresponding slot 38 so that the relative position of the links 32 and 34 can be varied.

Figure 9:
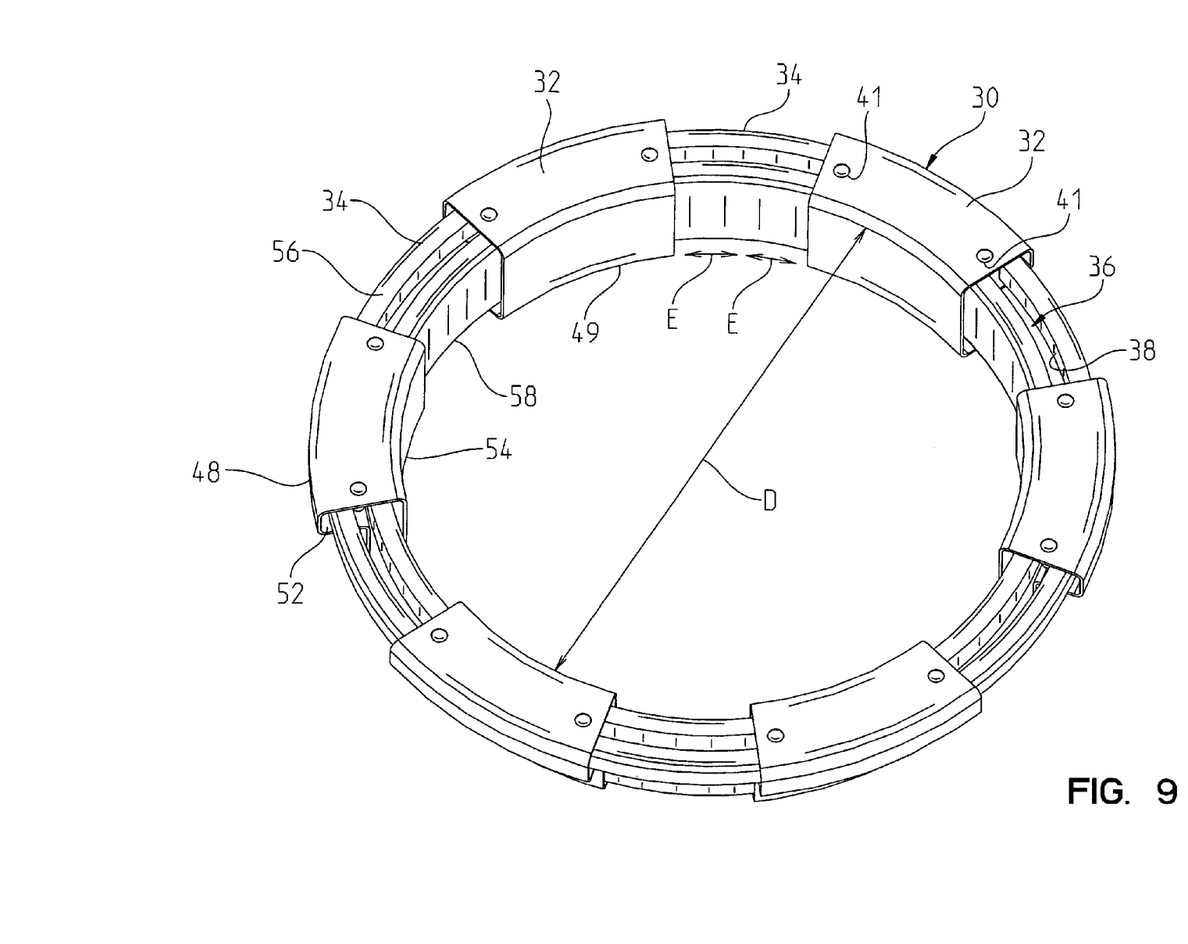
FIG. 9 is a top perspective view of a tissue protector according to a further embodiment of the invention.
Figure 10:
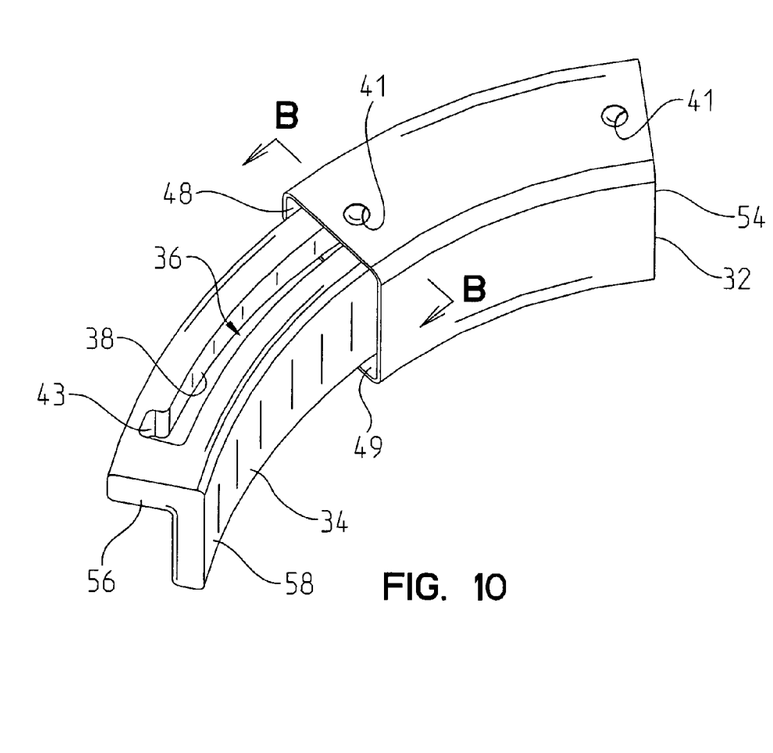
FIG. 10 is a perspective partial view of the tissue protector shown in FIG. 9.
Figure 11:
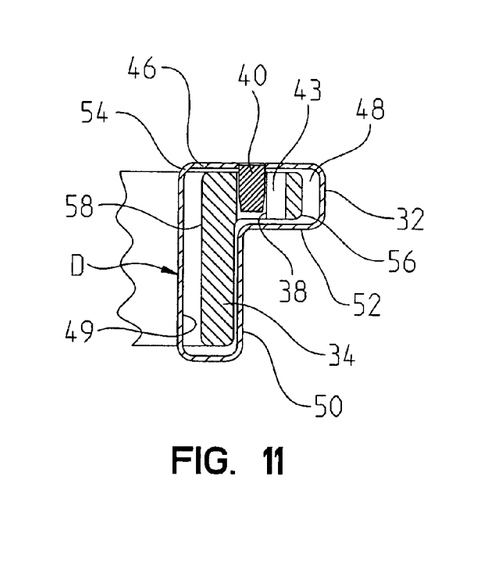
FIG. 11 is a side cross-sectional view of the tissue protector depicted in FIG. 10, taken along line B-B as viewed in the direction of the arrows.

In a preferred embodiment, each slot define a detent 43 at its opposite ends, as shown in FIGS. 10-11. The detent provides a resting position for the pins 40 at the ends of the slots 38 so that the pins, and ultimately the links, cannot be dislodged once engaged. The links 34 are arranged so that pressure from the interior of the incision bears against the links 34 to push then inwardly along the diameter D (FIG. 9). When the links 34 move in this direction, the detents 43 move to receive the pins 40 when the first set links 32 are situated at the ends of the second set links 34. Manual outward pressure against a second set link 34 will dislodge the pin from the detent to allow the link construct to be reduced for removal or adjustment to another convenient position as defined by the surgeon.

As best illustrated in FIG. 11, the links 32 and 34 are generally L-shaped. The links 32 are in the form of an L-shaped tubular body 46 with an upper channel 48 and a lower channel 49. The bores 41 open into the upper channel 48. The second set links 34 are also L-shaped with an upper leg 56, configured to slide within the upper channel 48, and a lower leg 58 configured to slide within the lower channel 49. As shown in FIG. 11, the tubular body 46 has a radial width greater than the thickness of the lower leg 58 so that the link 34 can shift diametrically inward to lock the pins 40 within the detents 43.

The tissue protector device 30 is configured to be positioned within an incision and expanded as the incision is retracted. The links 32 define an incision facing surface 50 that contacts the soft tissue within the incision, and a skin facing surface 52 that rests on the skin adjacent the incision. The skin facing surface can include a layer or topical film to reduce the sliding friction between the skin and the link as the tissue protector device 30 is expanded. In this regard, this embodiment can be considered to have a first portion configured to be supported on the body tissues surrounding the incision—i.e., the skin facing surface 52—and a second portion configured to cover the body tissues within the incision—i.e., the incision facing surface 50.

In addition to covering and protecting the body tissues within and around the incision, the device 30 also provides means for dissipating forces applied by a surgical tool or instrument. The L-shaped links 32 provide a corner against which the tools and instruments can bear. Any load applied to an L-shaped links is dissipated through the length of the link, as well as through the other inter-connected components of the device 30, to thereby reduce localized loading of the body tissues at the incision.

The tissue protector 30 of FIGS. 9-11 can be formed of various medical grade materials and can be made to be reusable or disposable. In the former instance, the links 32, 34 can be formed of stainless steel that can be sterilized according to known processes. Where the tissue protector is to be disposable, the components can be formed of a plastic material, such as polyurethane, appropriately sterilized for use in the arena.

Figure 12:
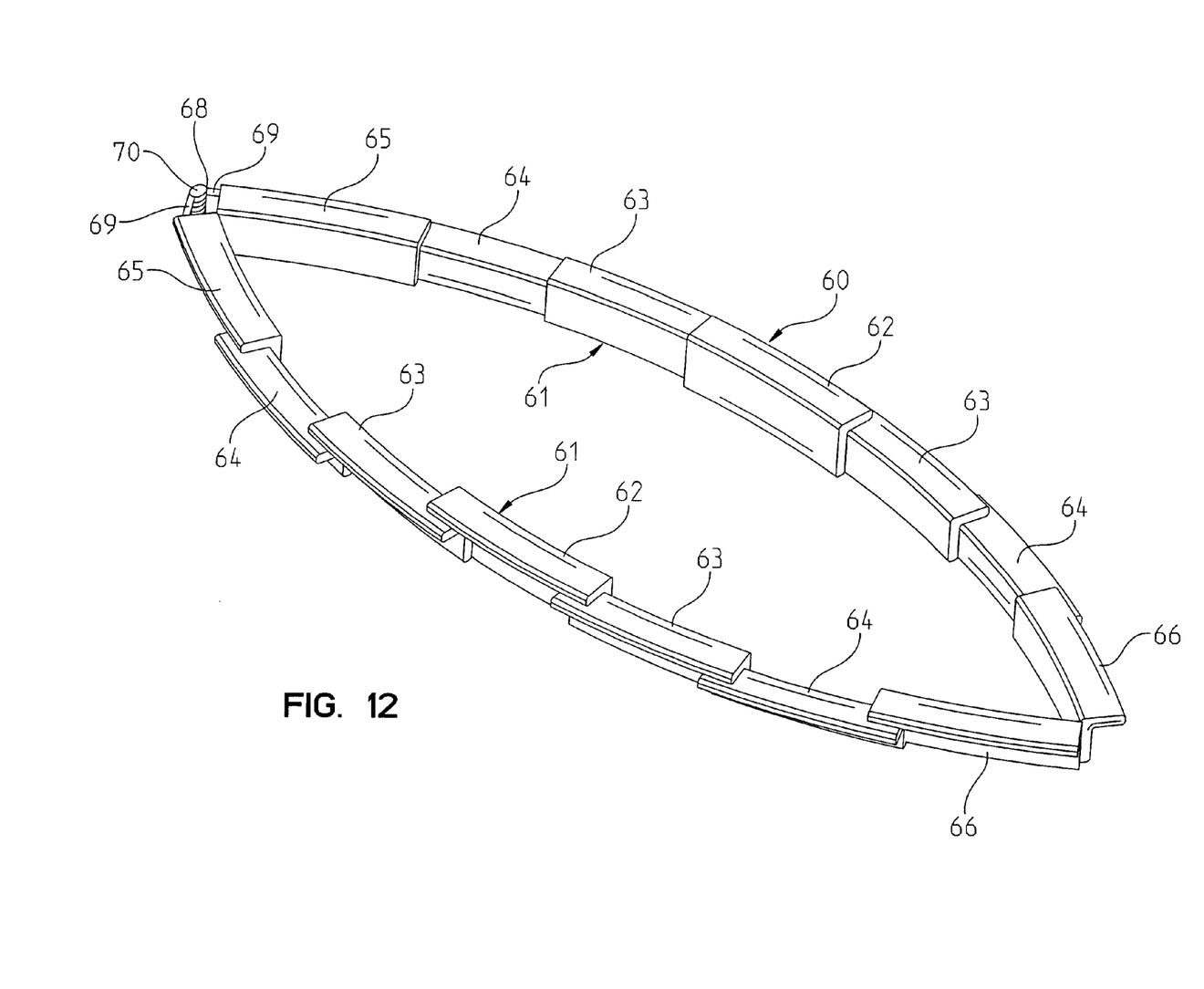
FIG. 12 is a top perspective view of a modified version of the tissue protector shown in FIG. 9.

The tissue protector device 60 shown in FIG. 12 employs an expanding link concept similar to that of the embodiment in FIGS. 9-11. In this embodiment, the tissue protector device 60 is formed by at least two opposing arc segments 61 While the device 30 of FIG. 9 is restricted to a circular shape, the arc segments 61 of the device 60 can be combined to form an oval or elliptical shape. The device 60 includes a plurality of sets of extendable links 62, 63, 64 and 66. Certain of these sets of links can be configured like the links 32 of FIG. 9 and others can be configured like the links 34. The links 62-64 include means for permitting expansion of the distance between the links, to thereby expand the perimeter of the tissue protector device 60. For example, the links 63 and 64 can include an L-shaped tubular body similar to the tubular body 46, and include the pins 40. The links 62 and 64 can include a slot and detent arrangement, like the slot 38 and detent 43, to receive the pin while in sliding engagement within the tubular body of the other sets of links. It can be appreciated that the tissue protector device 60 shown in FIG. 12 can accommodate transverse as well as longitudinal expansion of the surgical opening or incision.

In one aspect of the device 60, the end links 66 of the opposite arc segments 61 are connected by a hinge, at least at one end of the device. The hinge 70 includes arms 69 affixed to the opposite end links 66. The arms are pivotably connected to a pivot post 69 that allows for variable angular relationships between the arc segments 61. In the preferred embodiment, the arms 69 are resiliently biased to exert an opening force on the hinge, and consequently the arc segments 61. The hinge 68 can incorporate a torsion spring operable to separate the arms. Alternatively, the arms 69 of the hinge 68 can be formed of a shape memory material, such as NITINOL®, that assumes its "programmed" shape at expected temperatures.

Figure 13:
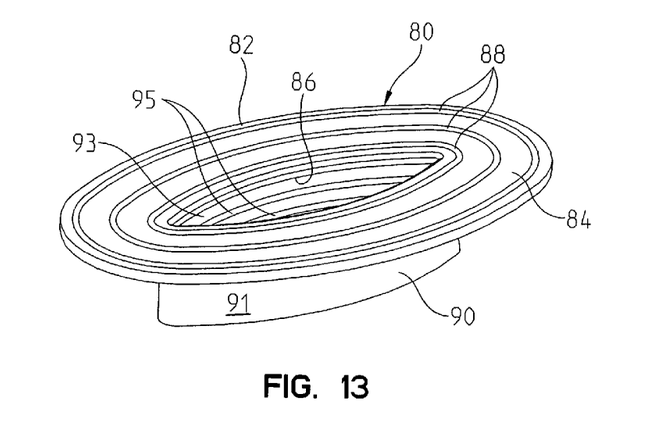
FIG. 13 is a top perspective view of a tissue protector according to a further embodiment of the invention.
Figure 14:
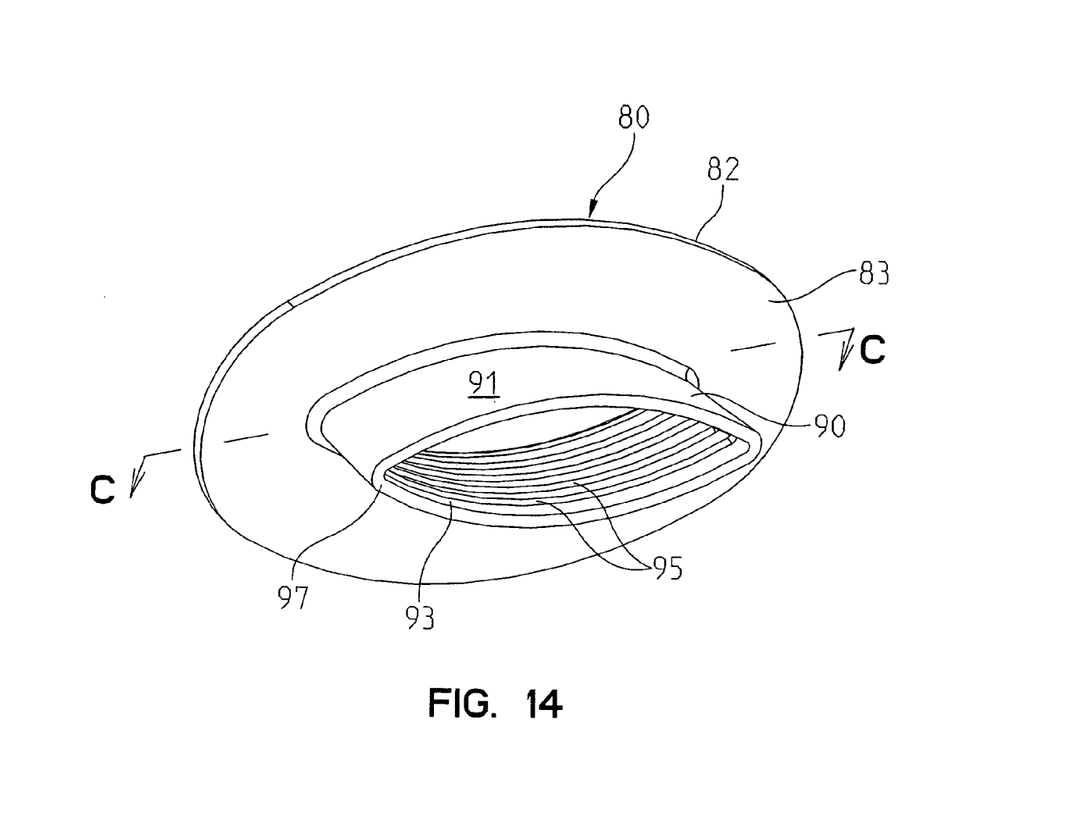
FIG. 14 is a bottom perspective view of the tissue protector shown in FIG. 13.
Figure 15:
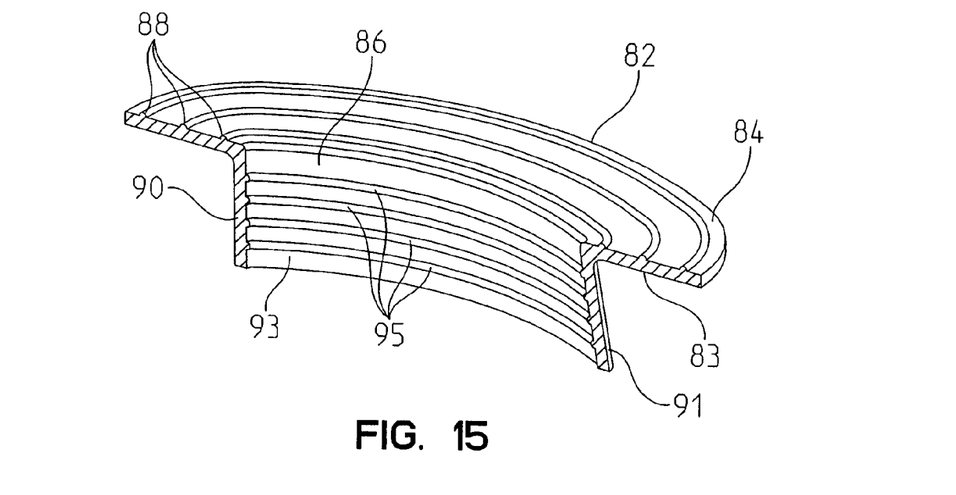
FIG. 15 is a side cross-sectional view of the tissue protector shown in FIG. 14, taken along line C-C as viewed in the direction of the arrows.

Referring now to FIGS. 13-15, a tissue protector 80 according to a further embodiment of the invention is depicted. The tissue protector 80 includes a flexible panel 82 that is configured to rest on the skin surrounding an incision. The panel includes a facing surface 83 that is adapted to be supported on the skin. As with the embodiment of FIGS. 2-8, the facing surface 83 can include a self-adherent layer that is adapted to adhere to the skin or to an antiseptic film applied to the skin.

In one feature of this embodiment, the upper surface 84 of the panel 82 defines a central opening 86 and a series of concentrically disposed ribs 88 projecting from the upper surface. The central opening 86 is preferably oblong or elliptical in shape to emulate the shape of the incision, as are the concentric ribs 88. The ribs act to absorb or dissipate force applied to the upper surface 84 by a surgical instrument T or retractor R. In addition, the ribs add hoop strength to the flexible panel 82, and consequently the underlying soft tissue, as the panel opening 86 is extended by tissue retractors. The flexible panel 82 is formed of a biocompatible elastomeric material, such as a silicone rubber like the SILASTIC® product manufactured by Dow Corning Inc. Other bio-compatible and sterilizable elastomeric materials are contemplated, such as neoprene, provided the material exhibits sufficient elasticity to expand laterally with the incision as the incision is retracted. Moreover, the material must be sufficiently wear resistant to avoid erosion or tearing under pressure or frictional contact with surgical tools and instruments. In related embodiments, the panel 82 can be made of a composite of different materials to accommodate varying elongation of the incision.

Preferably, the flexible panel 82, and particularly the opening 86, is provided in several sizes to accommodate different lengths of incisions. A particular tissue protector 80 can be selected based on the anticipated length of the incision—i.e., 2 inches, 5 inches, etc. The flexible panel 82 preferably has an oblong or elliptical shape, like the opening 86, extending 2-3 inches outward from the opening.

In a further feature of the tissue protector 80, a flexible sleeve 90 extends from the facing surface 83 of the flexible panel, as best seen in FIG. 14. The sleeve 90 is substantially co-extensive with the opening 86, as seen in FIG. 15. In the preferred embodiment, the sleeve is integrally formed with the panel so that the tissue protector 80 constitutes a one-piece device. Thus, the sleeve 90 is formed of the same material as the flexible panel and exhibits the same elastic properties. In related embodiments, the tissue protector 80 can be made of a composite of different materials for the panel 82 and the sleeve 90 to accommodate varying elastic properties required during a surgery.

The sleeve 90 is configured to reside within the incision in contact with the soft tissue under the skin. Thus, the sleeve 90 includes a facing surface 91 that presents a smooth, non-irritating surface to avoid trauma to the surrounding soft tissue. The facing surface 91 can be coated with an antiseptic layer. Like the flexible panel 82, the flexible sleeve 90 is configured to expand transversely with the incision as the incision is retracted.

The sleeve 90 will be interposed between any surgical instrument or tool, such as a tissue retractor R, and the soft tissue within the incision to protect this tissue from pressure-related trauma. The interior surface 93 of the sleeve is provided with interior ribs 95 similar to the ribs 88 on the flexible panel 82. The ribs help dissipate the force of tools and instruments when bearing against the sleeve. It is also contemplated that the lower edge 97 of the sleeve will be rounded to reduce the potential for soft tissue trauma as the sleeve is inserted into the incision. The sleeve 90 may also be slit vertically at strategic locations to allow for different expansions of the incision along its length.

The depth of the sleeve 90 can be calibrated to the depth of the exposure needed for the procedure. This depth depends upon the surgical site and the patient's anatomy. For instance, a hip replacement procedure will require exposure at a significant distance below the skin to permit visualization of the bony landmarks of the hip. This distance can be greater for patients having greater body mass indexes. For most surgical procedures, the depth of the sleeve 90 from the facing surface 83 of the panel 82 ranges between 2-6 inches. Of course, the size and configuration of the sleeve will be adapted to various other anatomic sites, such as the knee, shoulder, ankle, elbow, etc.

As seen in FIG. 15, the sleeve 90 is flared slightly outward away from the opening 86. This flare helps push the adjacent soft tissue away from the exposure site, especially as the incision is retracted and the surgical tools are inserted into the incision I during surgery.

In the surgical method of this embodiment of the invention, it is contemplated that the incision will be made at the surgical site once the site has been properly prepared. Once the length of the incision and the anticipated exposure depth has been determined, a tissue protector 80 is selected with an appropriately sized opening 86 and sleeve 90. The sleeve is carefully introduced into the incision until the flexible panel 82 contacts the skin surrounding the incision. If the panel includes an adherent facing surface, the panel is pressed against the skin until the panel adheres.

Tissue retractors are then introduced into the opening 86 and used to expand the opening while retracting the soft tissue at the incision. Once the incision has been retracted, surgical tools and instruments are advanced through the protected opening, using the tissue protector 80 as a bearing or fulcrum surface without fear of damaging the skin and soft tissue within the incision.

The invention also contemplates the use of certain known organ retractors at the incision site. One organ retractor that is suitable for use as a wound protector is a single use, vacuum activated bag, such as the SPACE-OR™ organ retractor sold by Advanced Surgical Concepts of Wicklow, Ireland. The SPACE-OR™ organ retractor is sold for use in abdominal surgery and is placed within the abdomen around bodily organs. The device includes a flat PVC bag filled with a malleable material. In its relaxed state, the organ retractor is formable into a variety of positions. When a vacuum is drawn in the bag, the device becomes rigid due to the compression of the bag and the internal malleable sheets. When the SPACE-OR™ organ retractor is deflated within the abdomen, it acts as a dam to hold adjacent organs away from the incision.

In the context of the present invention, an organ retractor, such as the SPACE-OR™ organ retractor, is positioned to overlap the incision with a portion of the organ retractor disposed inside the incision. With the organ retractor in its malleable or formable condition, conventional tissue retractors are used to retract the incision and the organ retractor. Once the incision has been fully retracted, a vacuum is drawn in the organ retractor to force it into its rigid state encircling the incision. In this rigid state, the SPACE-OR™ organ retractor protects the edge and interior of the incision and provides a surface to support surgical tools and instruments, in the same manner as the tissue protector 80 described above. Moreover, the use of the organ retractor as a tissue protector in accordance with this invention helps dissipate the concentrated forces exerted by surgical instruments on the incision into circumferential forces around substantially the entire perimeter of the incision.

Figure 16:
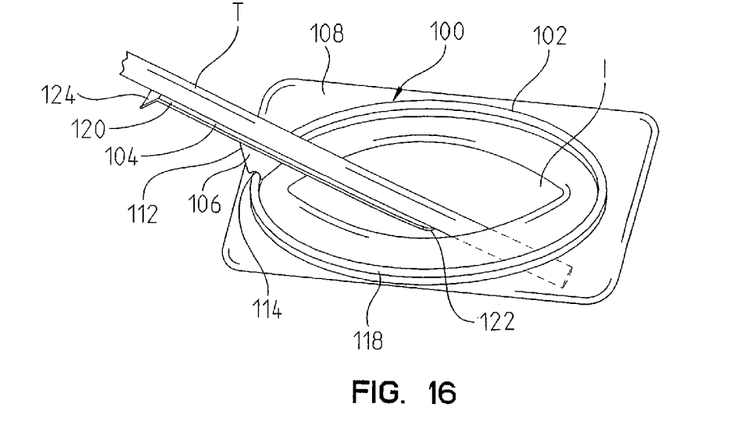
FIG. 16 is a top perspective view of a tissue protector according to yet another embodiment of the invention, depicted adjacent a surgical incision.
Figure 17:
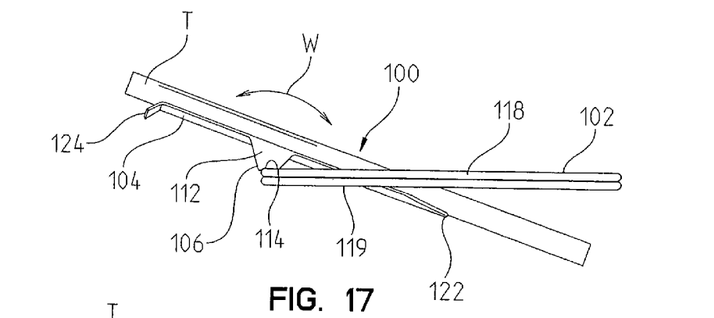
FIG. 17 is a side view of the tissue protector illustrated in FIG. 16.
Figure 18:
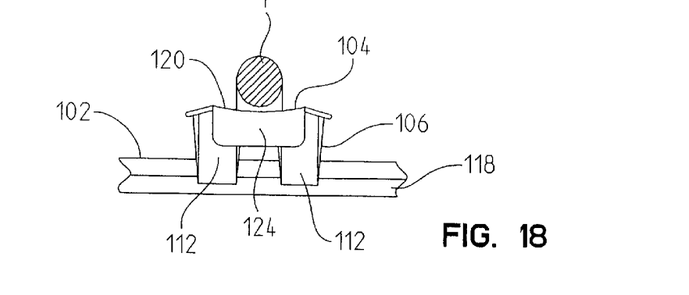
FIG. 18 is a partial end view of the tissue protector shown in FIGS. 16-17.

Yet another embodiment of the invention resides in a tissue protector device 100 illustrated in FIGS. 16-18. The device includes a track 102 that is sized to encircle a surgical incision. The track is preferably formed of a flexible material that can be arranged to conform to the general periphery of the incision before and/or after it has been retracted. The track 102 must also allow for proper conforming to the patient's anatomy at the surgical site. The device 100 includes an instrument support platform 104 and means 106 for slidably supporting the platform on the track 102.

The device 100 can include means 108 for fixing the location of the track 102 relative to the incision. In one embodiment, this means includes an self-adherent panel affixed to the track 102 and adapted to removably adhere to the skin surrounding the incision I. Other means are contemplated, such as taping or suturing the track to the skin, provided that the means can maintain the position of the track 102 relative to the incision. The means can also encompass a connector to connect the ring to tissue retractors already in position retracting the incision.

In a preferred embodiment of the invention, the means 106 for slidably supporting includes a pair of brackets 112 at the underside of the platform 104. The brackets each define a notch 114 that substantially conforms to an upper portion 118 of the track. The notch allows the platform to slide around the perimeter of the track 102. In one aspect, the upper portion 118 is in the form of a continuous ring, and the notch 114 is generally circular to correspond to the shape of the ring. In this regard, the means 106 can include means for pivotably supporting the platform 104 on the track 102. In particular, the platform can pivot or swivel, as shown by the arrows W in FIG. 17, so that the angle of the platform relative to the plane of the track 102 can be varied.

The platform 104 is configured to slidably support a surgical tool or instrument T. The platform can include an arcuate support surface 120, as best seen in FIG. 18. The arcuate surface helps hold the instrument on the platform when it is being manipulated. The support surface 120 can adopt other radii of curvature or other configurations, including channel shaped or tubular, to accommodate a particular surgical instrument. In one feature of this embodiment of the invention, the support surface 120 behaves like a cradle for the instrument while it is being used. The proximal end of the platform 104 includes a deflector panel 124 that is oblique to the support surface 120. The deflector panel 124 acts as an initial guide when an instrument T is placed on the platform 104. The deflector panel 124 also serves as a handle to allow the surgeon to reposition the platform 104 during the surgical procedure.

In order to reduce the likelihood of trauma to the soft tissue within the incision, the lower edge 122 of the platform 104 is rounded. Similarly, the lower portion 119 of the track 102 is rounded to avoid blunt trauma to the skin. The lower edge 122 of the platform is also flared laterally to allow for lateral movement of the tool or instrument on the platform within the incision I during the surgical procedure. The ability to move the toll or instrument within the incision is an important feature that allows the surgeon to properly prepare and position the patient's bone during a joint procedure.

In the method of use, an incision I is made at the surgical site. The tissue protection device 100 is positioned so that the track 102 substantially evenly encircles the incision. The incision can be retracted before or after the track 102 has been positioned on the skin. If the incision is retracted after the track has been placed, the track must be held in place at the site so that the track 102 can act as a support for the tissue retractors.

Once the incision I has been retracted and the bony landmarks exposed, a platform 104 can be mounted on the upper portion 118 of the track. The platform can slide around the periphery of the track to optimally position the surgical tool T supported by the platform. An additional platform 104 can be mounted on the track to provide a support and guide for another surgical instrument. The platforms 104 can be moved about the track 102 as necessary during the surgical procedure.

The lower edge 122 of the platform is lowered into the incision approximately to the position at which the tool would touch the bony surface. The platform now has isolated all the surrounding tissue from the bone. Thus, when the tool is used, the potential for damage to the adjacent tissue is significantly diminished.

The track 102 and platform 104 can be formed of a medical grade plastic or metal. The brackets 112 can be formed of the same material as the platform, or most preferably of a resilient plastic material, such as DELRIN®. The choice of material can dictate whether the tissue protector device 100 is disposable or reusable, since reuse requires re-sterilization of the device.

The platform 112 helps to support the tool during a surgical procedure. The arcuate shape helps dissipate the forces applied through the tool on the patient over a larger perimeter or area, thereby reducing the stress experienced by the skin and the edges of the incision. Selection of the length of the platform 112, the distance between the deflector panel 124 and the distal tip 122 is dependent upon the patient's anatomy, including joint dimensions and tissue dimensions at the surgical site. The particular surgical tool involved may also guide the selection of the particular platform. The present invention contemplates use with a variety of surgical tools and instruments, including turning tools such as drills and reamers. The dimension of the platform is particularly important with these type of tools to prevent any contact between the turning tool and the soft tissue within or without the incision. Other tools, such as broaches, benefit from the support and isolation offered by a properly sized platform 112.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method for protecting tissue at an incision for minimally invasive surgery comprising the steps of:
   making an incision at the surgical site;
   adhering an abrasion-resistant sheet of material to skin surrounding the incision, the abrasion-resistant sheet defining an elongated slot, the abrasion-resistant sheet being adhered such that the elongated slot is substantially coincident with the incision and such that the abrasion resistant sheet of material does not penetrate the incision during the application; and
   expanding the incision and the elongated slot to access the surgical site while the sheet of abrasion-resistant material is adhered to the skin surrounding the incision.

2. The method for protecting tissue of claim 1, wherein the step of adhering a sheet of material includes adhering the sheet of material to a betadiene layer applied to the skin surrounding the incision.

3. The method for protecting tissue of claim 1, further comprising the step of supporting a surgical tool on the abrasion-resistant sheet while manipulating the tool.

4. The method for protecting tissue of claim 1, further comprising the step of providing an anti-infection compound to the sheet of material.

5. The method of claim 1, further comprising:
   inserting a portion of the adhered sheet into the incision.

6. The method of claim 5, wherein the expanding comprises:
   applying force to the inserted portion of the sheet with a surgical instrument to expand the incision and the elongated slot of the adhered sheet of material to access the surgical site.

7. A tissue protector for use in minimally invasive surgery comprising:
   a sheet of abrasion-resistant material defining an elongated opening for access to a tissue incision, said sheet having an adherent facing surface through which said elongated opening extends, said adherent facing surface including an adhesive layer surrounding said elongated opening that is adapted to adhere said adherent facing surface to the surgical site surrounding the incision, wherein said sheet includes an expandable portion spanning said elongated opening at opposite ends thereof, wherein said expandable portion includes a pleat.

8. The tissue protector of claim 7, wherein said sheet includes reinforcements at the opposite ends of said elongated opening, said reinforcements comprising beads of the abrasion-resistant material.

9. The tissue protector of claim 7, wherein said sheet is dosed with an anti-infection compound.

10. The tissue protector of claim 7, wherein said sheet further includes a bead defined around at least a portion of said opening, said bead arranged to support a surgical tool or instrument extending into the incision when the sheet is applied to the surgical site.

11. The tissue protector of claim 7, wherein said sheet of material is anisotropic.

12. The tissue protector of claim 11, wherein said sheet of material exhibits greater resistance to stretching along an axis parallel to the length of said elongated opening than along an axis perpendicular to said length.

13. A tissue protector for use in minimally invasive surgery comprising:
   a sheet of abrasion-resistant material defining an elongated opening having terminal ends for access to a tissue incision, said sheet having an adherent facing surface through which said elongated opening extends, said adherent facing surface including an adhesive layer surrounding said elongated opening that is adapted to adhere said adherent facing surface to the surgical site surrounding the incision, wherein said sheet includes an expandable portion spanning said elongated opening at opposite ends thereof, wherein said expandable portion is configured to expand less toward the terminal ends of the opening.

14. The tissue protector of claim 13, wherein said sheet further includes a bead defined around at least a portion of said opening, said bead arranged to support a surgical tool or instrument extending into the incision when the sheet is applied to the surgical site.

15. The tissue protector of claim 13, wherein said sheet of material is anisotropic.

16. The tissue protector of claim 15, wherein said sheet of material exhibits greater resistance to stretching along an axis parallel to the length of said elongated opening than along an axis perpendicular to said length.

17. The tissue protector of claim 13, wherein said sheet includes reinforcements at the opposite ends of said elongated opening, said reinforcements comprising beads of the abrasion-resistant material.

18. The tissue protector of claim 13, wherein said sheet is dosed with an anti-infection compound.

* * * * *